US007917303B2

(12) United States Patent
Vanet et al.

(10) Patent No.: US 7,917,303 B2
(45) **Date of Patent: *Mar. 29, 2011**

(54) METHOD FOR IDENTIFYING COMBINATIONS OF MOTIFS THAT DO NOT MUTATE SIMULTANEOUSLY IN A SET OF VIRAL POLYPEPTIDE SEQUENCES COMPRISING A PUTATIVE DRUG BINDING SITE

(75) Inventors: Anne Vanet, Paris (FR); Michaela Muller-Trutwin, Paris (FR); Thomas Valère, Saint Leu-la-Foret (FR); Sophie Brouillet, Paris (FR); Emmanuelle Ollivier, Clamart (FR); Laurent Marsan, Feucherolles (FR)

(73) Assignee: Centre National de la Recherche Scientifique—CNRS (FR)

( * ) Notice: Subject to any disclaimer, the term of this patent is extended or adjusted under 35 U.S.C. 154(b) by 127 days.

This patent is subject to a terminal disclaimer.

(21) Appl. No.: 11/480,014

(22) Filed: Jun. 30, 2006

(65) Prior Publication Data

US 2007/0020619 A1 Jan. 25, 2007

Related U.S. Application Data

(63) Continuation-in-part of application No. 10/734,023, filed on Dec. 11, 2003, now Pat. No. 7,734,421, which is a continuation of application No. PCT/FR02/02068, filed on Jun. 14, 2002.

(60) Provisional application No. 60/696,597, filed on Jul. 5, 2005.

(30) Foreign Application Priority Data

Jun. 14, 2001 (FR) ..................................... 01 07808

(51) Int. Cl.
*G01N 33/48* (2006.01)

(52) U.S. Cl. ........................................... 702/20; 720/19

(58) Field of Classification Search ........................ None
See application file for complete search history.

(56) References Cited

U.S. PATENT DOCUMENTS 7,734,421 B2 * 6/2010 Vanet et al. ..................... 702/19

FOREIGN PATENT DOCUMENTS

WO WO 99/61658 12/1999

OTHER PUBLICATIONS

Chou, K.-C., 1996, Prediction of Human Immunodeficiency Virus Protease Cleavage Sites in Proteins, Anal. Biochem. 233:1-14.*

Draghici, S., and R. B. Potter, 2003, Predicting HIV drug resistance with neural networks, Bioinformatics 19(1):98-107.*

Korber, B. T. M., et al., 1993, Covariation of mutations in the V3 loop of human immunodeficiency virus type 1 envelope protein: An information theoretic analysis, Proc. Natl. Acad. Sci. USA 90:7176-7180.*

Winslow, D. L., et al., 1995, Limited sequence diversity of the HIV type 1 protease gene from clinical isolates and in vitro susceptibility to HIV protease inhibitors, AIDS Res. Human Retrovir. 11(1):107-113.*

Zhang, L, et al., 1999, Quantifying residual HIV-1 replication in patients receiving combination antiretroviral therapy, The New Engl. J. of Med. 340(21):1605-1613.*

HIV Sequence Compendium, 2000, Kuiken, C. L., et al., eds., Theoretical Biology and Biophysics Group, Los Alamos National Laboratory, Los Alamos, NM, LA-UR 01-3860, pp. 480-483.*

Collins, J. F., and A. F. W. Coulson, 1987, Chapter 13: Molecular sequence comparison and alignment, in Nucleic acid and protein sequenc analysis a practical approach, IRL Press, Washington, DC, pp. 323-358.*

Stoll, V., et al., 2003, X-ray crystallographic structure of ABT-378 (lopinavir) bount to HIV-1 protease, Bioorganic & Medicinal Chemistry 10:2803-2806.*

Gonzalez, L. M. F., et al., 2003, In vitro hypersusceptibility of human immunodeficiency virus type 1 subtype C protease to lopinavir, Antimicrob. Agents and Chemother. 47(9):2817-2822.*

Brouillet, S., et al., 2010, Co-lethality studied as an asset against viral drug escape: the HIV protease case, Biol. Dir. 5-40-1-13.*

Robert W. Shafer et al., *Human immunodeficiency virus type I reverse transcriptase and protease mutation search engine for queries*, Nature Medicine, vol. 6, No. 11, Nov. 2000, pp. 1290-1292.

Rami Kantor et al., *Human Immunodeficiency Virus Reverse Transcriptase and Protease Sequence Database: an expanded data model integrating natural language text and sequence analysis programs*, Nucleic Acids Research, vol. 29, No. 1, Jan. 2001, pp. 296-299.

Robert W. Shafer et al., *Human Immunodeficiency Virus Reverse Transcriptase and Protease Sequence Database*, Nucleic Acids Research, vol. 28, No. 1, Jan. 2000, pp. 346-348.

Robert W. Shafer et al., *Human Immunodeficiency Virus Reverse Transcriptase and Protease Sequence Database*, Nucleic Acids Research, vol. 27, No. I, Jan. 1999, pp. 348-352. P. L. Wesche et al., "DNA Sequence Error Rates in Genbank Records Estimated Using the Mouse Genome as a Reference," *DNA Sequence*, Oct./Dec. 2004, vol. 15 (5/6), pp. 362-364.

C. B. Lawrence et al., "Assignment of Position-Specific Error Probability to Primary DNA Sequence Data," *Nucleic Acids Research*, 1994, vol. 22, No. 7. pp. 1272-1280.

(Continued)

*Primary Examiner* — Jeffrey S. Parkin
(74) *Attorney, Agent, or Firm* — DLA Piper LLP (US)

(57) ABSTRACT

Methods for identifying a motif or a combination of motifs having a Boolean state of predetermined mutations in a set of sequences including a) aligning a set of sequences of ordered motifs represented by a single-character code, b) comparing a reference sequence with the set of sequences aligned in step (a), c) identifying motifs not having mutated simultaneously and/or motifs having mutated simultaneously at least once on at least one sequence of the set and not having mutated on another sequence of the set.

15 Claims, No Drawings

OTHER PUBLICATIONS

Eddy, S., "Hidden Markov models," Curr. Opin. Struct. Biol., vol. 6. pp. 361-365, 1996.

Laurent-Puig, P. et al., "APC gene: database of germline and somatic mutations in human tumors and cell lines," Nucleic Acids Res Jan. 1, 1998; 26(1): pp. 269-270.

Beroud, C. et al., "p53 and APC gene mutations: software and databases," Nucleic Acids Res Jan. 1, 1997; 25(1), p. 138.

Papillon, E. et al., "A malignant gastrointestinal stromal tumor in a patient with multiple endocrine neoplasia type 1," European Journal of Gastroenterology & Hepatology, 2001, 13:207-211.

Gallou, C. et al., "Mutations of the VHL Gene in Sporadic Renal Cell Carcinoma: Definition of Risk Factor for VHL Patients to Develop an RCC," Human Mutation, 13:464-475 (1999).

Baudry, D. et al., "WT1 Splicing Alterations in Wilms' Tumors," Clin Cancer Res Oct. 2000; 6(10): pp. 3957-3965.

Hammond, J. et al., "Mutations in Retroviral Genes Associated with Drug Resistance," The Human Retrovirus and AIDS Compendium, 1999, pp. 542-591.

Chou, K.C., "Prediction of Human Immunodeficiency Virus Protease Cleavage Sites in Proteins," Anal. Biochem. 1996, 233, pp. 1-14.

Draghici, S. et al., "Predicting HIV drug resistance with neural networks," Bioinformatics, 19(1), 2003, pp. 98-107.

Rose, P. P. et al., "Detecting hypermutations in viral sequences with an emphasis on G→ A hypermutation," Bioinformatics, 2000, vol. 26, No. 4, pp. 400-401.

Strimmer, K. et al., "Likelihood-mapping: A simple method to visualize phylogenetic content of a sequence alignment," PNAS, Jun. 1997, vol. 94, pp. 6815-6819.

Caride, E. et al., "Sexual transmission of HIV-1 isolate showing G→ A hypermutation," Journal of Clinical Virology, 2002, vol. 23, pp. 179-189.

Collins, J. F. et al., "Chapter 13: molecular sequence comparisons and alignment In Nucleic acid and protein sequence analysis," IRL Press., 1987, pp. 232-358.

Zhang, L. et al., "Quantifying Residual HIV-1 Replication in Patients Receiving Combination Antiretroviral Therapy," New England Journal of Medicine, May 1999, vol. 340, No. 21, pp. 1605-1613.

Thompson, J. D et al., "CLUSTAL W: Improving the sensitivity of progressive multiple sequence alignment through sequence weighting, position-specific gap penalties and weight matrix choice," Nucleic Acids Research, 1994, vol. 22, No. 22, pp. 4673-4680.

Eddy, S., "Multiple Alignment and multiple sequence based searches," Trends Guide to Bioinformatics, 1998, pp. 15-18 (preprint).

* cited by examiner

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 1

Ser Val Arg Leu Gly His Lys Asp Glu Val
  1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 2

Ser Arg Arg Leu Gly His Lys Asp Glu Val
```

```
                               1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 3

Ser Val Arg Leu Gly His Lys Leu Glu Val
  1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 4

Ser Arg Asp Leu Gly His Lys Asp Glu Val
  1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 5

Ser Val Arg Leu Gly His Leu Asp Val Val
  1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 6

Ser Val Asp Leu Gly His Lys Thr Glu Val
  1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 7

Ser Lys Arg Leu Gly His Lys Asp Glu Val
  1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide
```

```
<400> SEQUENCE: 8

Ser Val Arg Leu Gly His Gly Asp Gly Val
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 9

Ser Val Arg Leu Gly His Lys Ser Glu Val
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 10

Val Thr Ile Lys Ile Gly Gly Gln Leu Lys
  1               5                  10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 11

Thr Ile Lys Ile Gly Gly Gln Leu Lys
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 12

Asp Thr Val Leu Glu Glu Met Ser Leu
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 13

Leu Val Gly Pro Thr Pro Val Asn Ile
  1               5

<210> SEQ ID NO 14
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      immunogenic peptide

<400> SEQUENCE: 14

Val Leu Val Gly Pro Thr Pro Val Asn Ile
1               5                   10

<210> SEQ ID NO 15
<211> LENGTH: 99
<212> TYPE: PRT
<213> ORGANISM: Human immunodeficiency virus

<400> SEQUENCE: 15

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Lys Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 16
<211> LENGTH: 99
<212> TYPE: PRT
<213> ORGANISM: Human immunodeficiency virus

<400> SEQUENCE: 16

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Pro Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 17
<211> LENGTH: 99
<212> TYPE: PRT
<213> ORGANISM: Human immunodeficiency virus

<400> SEQUENCE: 17

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30
```

```
Leu Glu Glu Met Ser Leu Pro Gly Arg Trp Lys Pro Lys Met Ile Gly
             35                  40                  45

Gly Ile Gly Gly Phe Ile Lys Val Arg Gln Tyr Asp Gln Ile Leu Ile
         50                  55                  60

Glu Ile Cys Gly His Lys Ala Ile Gly Thr Val Leu Val Gly Pro Thr
 65              70                  75                  80

Pro Val Asn Ile Ile Gly Arg Asn Leu Leu Thr Gln Ile Gly Cys Thr
                 85                  90                  95

Leu Asn Phe

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 18

Val Thr Leu Trp Gln Arg Pro Leu Val
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 19

Glu Glu Met Ser Leu Pro Gly Arg Trp
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      immunogenic peptide

<400> SEQUENCE: 20

Lys Met Ile Gly Gly Ile Gly Gly Phe Ile
 1               5                  10
```

METHOD FOR IDENTIFYING COMBINATIONS OF MOTIFS THAT DO NOT MUTATE SIMULTANEOUSLY IN A SET OF VIRAL POLYPEPTIDE SEQUENCES COMPRISING A PUTATIVE DRUG BINDING SITE

RELATED APPLICATION

This is a continuation-in-part of U.S. application Ser. No. 10/734,023, filed Dec. 11, 2003, which is a continuation of International Application No. PCT/FR02/02068, with an international filing date of Jun. 14, 2002, which is based on French Patent Application No. 01/07808, filed Jun. 14, 2001, and this application also claims the benefit of U.S. Provisional Application No. 60/696,597, filed Jul. 5, 2005, all of which are hereby incorporated by reference.

TECHNICAL FIELD

This disclosure pertains to the field of analysis of sequences of nucleotides and/or amino acids composing living organisms, in particular, analysis of particular mutations of the sequences.

The disclosure also pertains to methods of identification and selection of fragments of sequences of nucleic acids or proteins constituted by and/or comprising motifs having characteristics of specific mutability. The disclosure further pertains to pharmaceutical compositions containing the fragments that are useful for treating and/or preventing human, animal and/or plant pathologies or are useful for screening therapeutic compounds.

BACKGROUND

It is known that the mutations induced in the wild-type sequences of pathogenic organisms are responsible, for example, for therapeutic escape mechanisms, i.e., the capacity of viral or bacterial pathogenic organisms to resist a therapeutic treatment. The nucleotide and/or polypeptide sequences of the mutant strains of the organisms have particular mutations in relation to the nucleotide or polypeptide sequences of the wild-type strains.

Such mutations are also determinant of functional changes of the genes or proteins which have as a consequence the deterioration of numerous biological processes, such as the triggering of the immune response, infectivity of viruses, development of cancers, etc.

It is known, for example, that the genetic information of the human immunodeficiency virus (HIV), which belongs to the retrovirus family, is supported by two RNA molecules. Upon infection, integration of the viral genome with that of host cells can therefore not be implemented directly. The prior synthesis of a DNA copy from the genomic RNA of the virus is a determinant step of the infectious cycle. The enzyme responsible for this reverse transcription is a protein called Reverse Transcriptase (RT). The low reverse-transcriptional accuracy of this protein confers on the virus a large genomic variability. It is estimated that in an untreated serum-positive individual, one mutation appears per replication and, thus, for the ten billion viruses produced per day, there would be 10 billion new mutations. This mutation can lead to resistance to one or more antiretroviral agents and, thus, generate strains that are more virulent because they are increasingly resistant.

Faced with this problematic situation, practitioners prescribe very intense treatment regimens such as long-term triple drug combinations and, more recently, even quadruple drug combination and, perhaps even more in the future, profiting from the absence of resistant virus which characterize in general the patients who have not yet been treated and are infected by a single form of virus. These treatments then cause a strong diminution of the viral load, which is considered to be the quantity of viral particles circulating in the blood, the number of viral mutants which is directly proportional to the viral load diminishes as well, thereby reducing the risks of therapeutic escape.

These extremely intense treatments are unfortunately accompanied by numerous side effects. They moreover require perfect compliance which, if not respected, is accompanied almost systematically by the emergence of resistant strains. These selected resistances under the pressure of antiretroviral agents are at the origin of most of the therapeutic escapes.

Thus, although the choice of a combination of antiretroviral agents appears to be fundamental, the optimized combination of these agents does not appear to be obvious. In addition to the multiple problems posed by the resistances, which we have just described, the incompatibility of certain drug combinations and the constantly increasing number of antiretroviral agents makes the practitioner's work more and more difficult.

Physicians at present have available about twenty therapeutic agents essentially directed against two viral proteins—reverse transcriptase and protease. The most common therapeutic regimens involve triple drug combinations. A total of 252 possible combinations have been described—based only on the most common combinations. These calculations are statistical and do not take into account the different drug incompatibilities. Moreover, the appearance of new active ingredients stemming from pharmaceutical research will have the direct consequence of further complicating the problem of the selection of the drug combination.

The activity of other pathogenic organisms is also of concern: the flu virus was responsible for 20 million deaths during the $20^{th}$ century and the Ebola virus emerged in an alarming manner. The hepatitis A, B, C, D and E viruses constitute veritable public health priorities both because of their Boolean status and their potential gravity.

In all of these cases, there is a therapeutic and vaccinal vacuum which increases each year because of the great mutability of the viral genomes, especially that of the retroviruses, RNA viruses such as HIV, flu, Ebola, hepatitis C, etc.

Many approaches have been proposed for attempting to resolve these multiresistance problems linked with the high degree of mutability of certain pathogenic organisms. The company Virco Tibotech, for example, developed a method directed by a computer program that enables comparison of a given genotype with a databank of HIV sequences. It then defines a list of the possible resistances to the antiretroviral agents.

Moreover, certain web sites such as that of the Los Alamos Library provide a large amount of data regarding the alignments of the HIV protein sequences as well as their mutations. This Library is provided online by the Division of AIDS of the National Institute of Allergy and Infectious Diseases (NIAID), a part of the National Institutes of Health (NIH).

Similarly, many publications by Ribeiro et al. disclose methods employing the calculation of the Boolean status of the appearance of resistant mutants using rather complex mathematic calculations.

Thus, methods for identifying the mutations of the constituent motifs of nucleotide or polypeptide sequences have been developed, e.g., those that made it possible during the 1980s to classify the immunoglobulins into classes and subclasses comprising constant domains and variable domains as a function of the variability of motifs of the different sequences that comprised them.

However, these methods do not enable identification of motifs whose mutation possibility is predetermined in relation to the set of sequences analyzed. This mutation possibility corresponds to a Boolean state of mutation.

It would therefore be advantageous to provide for the identification of multiple motifs the Boolean state of relative mutation of which is predetermined in relation to a set of given sequences. This method should be based on the identification either of motifs or combinations of motifs not ever having had mutated simultaneously, or motifs or combinations of motifs having mutated simultaneously at least once on at least one sequence of a set and not having mutated on other sequences of the set.

SUMMARY

Selected aspects of this disclosure relate to methods for identifying a motif or a combination of motifs having a Boolean state of predetermined mutations in a set of sequences including a) aligning a set of sequences of ordered motifs represented by a single-character code, b) comparing a reference sequence with the set of sequences aligned in step (a), c) identifying motifs not having mutated simultaneously and/or motifs having mutated simultaneously at least once on at least one sequence of the set and not having mutated on another sequence of said set.

Another selected aspect relates to pharmaceutical compositions for treatment of influenza, HIV and hepatitis C including a therapeutically effective amount of the motif or combination of motifs.

Yet another aspect relates to methods of treating influenza, HIV and hepatitis C including administering a therapeutically effective amount of the pharmaceutical composition.

Still other aspects relate to methods of preparing oligonucleotide and polypeptide sequences.

DETAILED DESCRIPTION

We provide new tools to enable finding more durable solutions during therapeutic treatments of pathologies involving pathogenic organisms or human genes having a high degree of mutability.

We also provide for the use of sequences constituted by or comprising the motifs and/or combinations of motifs thereby identified for treating or preventing human, animal or plant pathologies, the preparation of therapeutic targets for the screening of said drugs, the docking of a drug on its target, the development of new diagnostic tools in which, for example, the selection of one or more therapeutic agents can be performed as a function of the mutability of the pathogenic organism responsible for the disease of a given patient.

The term "motif" as used herein is understood to mean a nucleotide capable of being part of a synthetic nucleic acid or oligonucleotide sequence designated below by its single-character code: A, G, C, T or U, corresponding to the nomenclature of the respective base (adenine A, guanine G, cytosine C or thymine T in the DNA, or uracil U in the RNA) of which they are constituted.

The term "motif" is also understood to mean an amino acid, irrespective of its configuration, capable of being part of a natural or synthetic protein or peptide, designated by its single-character code such as, e.g., represented in the table below.

Codes of the amino acids

| Code | Amino Acid |
|---|---|
| A | alanine |
| C | cysteine |
| D | aspartic acid |
| E | glutamic acid |
| F | phenylalanine |
| G | glycine |
| H | histidine |
| I | isoleucine |
| K | lysine |
| L | leucine |
| M | methionine |
| N | asparagine |
| P | proline |
| Q | glutamine |
| R | arginine |
| S | serine |
| T | threonine |
| V | valine |
| W | tryptophan |
| Y | tyrosine |

The term "sequence" is understood to mean any chaining of motifs as defined above capable of constituting a sequence of a nucleic acid or a fragment thereof of a living organism or a sequence of a protein or a fragment thereof of a living organism, including wild-type sequences, mutant sequences or artificial sequences similar to those obtained by chemical or biological synthesis according to methods known in the art. As nonlimitative examples, it is understood that a sequence containing such motifs can be a group of genes, a gene or a fragment thereof, a group of proteins, a protein or a fragment thereof.

The term "variant of a sequence" is understood to mean any sequence differing from the original or wild-type sequence by at least one motif.

Thus, we identified motifs that did not mutate simultaneously among all of the members of a set of sequences and/or motifs having mutated simultaneously at least once on at least one sequence of the set and not having mutated on another sequence of the set. The identification of such motifs is a major achievement among new pharmacological developments both in terms of therapeutic targets as well as at the level of the searching for new therapeutic compounds, especially in the framework of resistance and multiple-resistances developed by pathogenic organisms, which are harmful for both animal species as well as plant species.

As an example, we identified a motif or a combination of motifs indispensable for the function of a protein of a human, animal or plant organism or of a pathogenic organism. The proteins produced by mutant strains must conserve a particular structure to preserve their functions. Thus, when a mutation is associated with the loss of a specific function, geneticists search for a second mutation, which restores this specific function. This mutation's association reveals a "structural link" between both of these amino acids, the structural link corresponding to a specific function of the protein. Consequently, identification of the amino acids that mutate simultaneously on a specific protein allows identification of motifs potentially associated with specific function and thus of potential "therapeutic targets" on this protein.

As another example, we identified potential binding site for drugs. In fact, many drugs act as competitive inhibitors by their binding to the target protein. It is possible to evaluate the binding capacity of candidate molecules to the target protein when the 3D structure of the target protein is known. This modeling is called "docking." The main characteristic associated with the drug efficiency is then based on the drug—target protein interaction stability. Nevertheless, the efficiency of the identified drug may diminish if the amino acids of the drug binding site on the target protein mutate. Consequently, it is very important for developing new drugs with good and stable efficiency to identify the amino acids that do not mutate simultaneously on the target protein corresponding to the best binding site. Preferably, this binding site is associated or located in proximity with an identified therapeutic target on the protein for obtaining a more efficient drug.

As still another example, we identified new vaccine compositions. A vaccine has to contain different immunogenic peptides. Nevertheless, these immunogenic peptides can lose their vaccinal efficiency because of the important mutation rate of the related pathogenic organism. Consequently, it is very important when obtaining a vaccine with stable efficiency to identify immunogenic peptides combination containing amino acids that do not mutate simultaneously on the target protein.

Another aspect of the disclosure also pertains to the use of these fragments of sequences constituted by and/or comprising motifs that did not mutate simultaneously and/or motifs having mutated simultaneously at least once on at least one sequence of the set and not having mutated on another sequence of the set as therapeutic targets that are useful for screening drugs as well as for vaccines directed against pathogenic organisms and, in particular, against pathogenic organisms having a high degree of mutability.

Still another aspect of the disclosure further pertains to the use of sequences constituted by and/or comprising motifs that did not mutate simultaneously and/or motifs having mutated simultaneously at least once on at least one sequence of the set and not having mutated on another sequence of the set for screening compounds useful for preventing and treating human and/or animal pathologies, and in particular pathologies the responsible genes of which have a high degree of mutability.

The use of fragments of particular sequences of the pathogenic organisms constituted by and/or comprising the motifs that did not mutate simultaneously or motifs having mutated simultaneously at least once on at least one sequence of the set and not having mutated on another sequence of the set as therapeutic compounds makes it possible, among other things, to:

Decrease the appearance of resistances during therapeutic treatment;

Stabilize the health of the patient over the long term by permitting the use of the drugs available on the market for a longer period of time;

Avoid the appearance of opportunistic diseases and thereby decrease the overall cost of the treatment;

Decrease the duration and the cost of investments in research and development in the pharmaceutical industry.

We thus provide a new tool for optimizing selection of therapeutic treatments directed against pathogenic organisms with a high degree of mutability or against pathologies due to the appearance of mutations.

One aspect of the methods for identifying motifs comprises comparing a subset of variants of the same nucleotide or polypeptide sequence of a given pathogenic organism by a reference sequence, for example, a consensus sequence, and then identifying during this comparison the motifs of the sequences which did not mutate simultaneously or the motifs which mutate simultaneously at least once on at least one of the sequences of the subunit and do not mutate on the other sequences of the subunit.

We more precisely provide methods for identifying a motif or a combination of motifs having a Boolean state of predetermined mutation in a set of sequences, comprising:

a) alignment of sequences of ordered motifs represented by their single-character code, b) comparison of a reference sequence with the set of sequences aligned in step (a), c) identification of the motifs that did not mutate simultaneously and/or of the motifs having mutated simultaneously at least once on at least one of the sequences of the set and not having mutated on the other sequences of the set.

According to one embodiment, the motif or the combination of motifs to be identified is a nucleotide or a combination of nucleotides and the subset of sequences can be extracted from a databank of nucleic acids.

According to another embodiment, the motif or the combination of motifs to be identified is an amino acid or a combination of amino acids and the subset of sequences can be extracted from a databank of polypeptides and/or proteins.

According to a particular aspect, the methods further comprise the step of d) selecting the motifs, wherein the amino acids are distant from less then 20 Angstroms, preferably from less than 15 Angstroms and more preferably from less than 10 Angstroms. This allows the identification of motifs corresponding to potential therapeutic target and/or of potential drug binding site for docking.

According to another particular aspect, the methods comprise the step of d) selecting at least two immunogenic peptides, preferably at least three immunogenic peptides and more preferably at least four immunogenic peptides each comprising one different amino acid of one identified motif.

Immunogenic peptides derived from a specific pathogenic organism can be simply identified by methods well known from one of skilled in the art. Examples of immunogenic peptides are provided online by the Division of AIDS of the National Institute of Allergy and Infectious Diseases (NIAID), a part of the National Institutes of Health (NIH).

For example, when the number of sequences of the subset that is being used is less than 100, it is possible to use the alignment method of Clustal W. (Thompson, J. D., Higgins, D. G. and Gibson, T. J. (1994) CLUSTAL W: Improving the sensitivity of progressive multiple sequence alignment through sequence weighting, position-specific gap penalties and weight matrix choice. Nucleic Acids Research, 22: 4673-4680).

If the number of sequences to analyze is larger, e.g., greater than 100, the alignment proposed by Clustal W. is too long and it is necessary to employ an iterative alignment based on a hidden Markov model, referred to below as HMM (Sean Eddy, "Hidden Markov Models", Curr. Opin. Struct. Biol. Vol. 6, pages 361-365, 1966).

In this latter case, there is created, for example, a first subset of 100 sequences extracted from the set of sequences to be analyzed to which is applied the Clustal method to obtain a first alignment.

A hidden Markov model (HMM) is created from this first alignment. The model is possibly calibrated to make it more sensitive, then one adds to the first alignment new sequences which will in turn be aligned again using HMM.

The reference sequence of step (b) is advantageously constituted by a wild-type sequence or by a consensus sequence comprising in position i the motif present in position i in a predetermined number of sequences of step (a), for example, in more than 30% of said sequences and more preferably in more than 75% of said sequences, with it being possible to adjust these values according to the case.

Step (b) comprising comparison of sequences of the identification method of the disclosure advantageously comprises:

constituting a first numerical matrix A of dimensions N×M in which N designates the number of sequences and M designates the number of motifs of one of the sequences of said alignment, with the value $A_{i,j}$ being equal to a first value A1 [for example, "0"] when the motif of position i of the sequence j is mutated in relation to the motif of position i of the reference sequence and equal to a second value A2 [for example, "1"] in the other cases, constituting two analysis matrices B and C of the mutations in which the matrices are:
a matrix B of unmutated couples, i.e., of couples which did not mutate simultaneously, of dimension M×M, the value $B_{i,k}=B_{k,i}$ being equal:
to a first value B1 [for example, "0"] when $A_{i,j}=A_{k,j}=A1$ irrespective of the value of j ranging from 0 to N,
to a second value B2 [for example "1"] in the other cases;
a matrix C of mutated couples [i.e., of couples that mutate either always, or never simultaneously] of dimension M×M, the value $C_{k,i}=C_{i,k}$ being equal:
to a second value C1 [for example, "1"] when $A_{i,j}=A_{k,j}$ irrespective of the value of j ranging from 0 to N,
to a first value C2 [for example, "0"] in the other cases;
of determining for a set E of positions a coefficient $R_E$ whose value is $R_1$ [for example, "1"] when the values $B_{i,k}$ are equal to the second value $B_2$, irrespective of the values of i and k belonging to the set E of the positions,
of determining for a set F of positions, a coefficient $R_F$, the value of which is $R_1$ [for example, "1"] when the values $C_{i,k}$ are equal to the second value C1, irrespective of the values of i and k belonging to the set F of the positions.

According to one embodiment, in step (b) of the method, the positions of the sets E and/or F are designated by the user.

According to another embodiment, step (b) of the method comprises a test step of generating a totality of the combinations of the possible positions and determining for each of the combinations the value of the coefficients $R_E$ or $R_F$, and of retaining the combination corresponding to the largest set of positions of which $R_E$ or $R_F$ correspond to the second value.

The matrix of mutated couples of the disclosure advantageously makes it possible to identify two motifs having mutated simultaneously at least once on at least one of the sequences of the set and not having mutated on the other sequences of the set.

We also found ways to perform comparisons of the sequences containing the motifs and identifying the motifs thereof, either having mutated simultaneously at least once on at least one of the sequences of the set and not having mutated on the other sequences of the set and comprising:

constituting a first numerical matrix A of dimensions N×M in which N designates the number of sequences and M designates the number of motifs of one of the sequences of the alignment, the value $A_{i,j}$ being equal to a first value $A_1$ [for example, "0'] when the motif of position of the sequence j is mutated in relation to the motif of position i of the reference sequence and equal to a second value $A_2$ [for example, "1"] in the other cases,
constituting two analysis matrices B and C of the mutations M in which this matrix is:
a matrix B of unmutated couples, i.e., couples which did not mutate simultaneously, of dimension M×M, the value $B_{i,k}=B_{k,i}$ being equal:
to a first value B1 [for example, "0"] when $A_{i,j}=A_{k,j}=0$ irrespective of the value of j ranging from 0 to N,
to a second value B2 [for example, "1"] in the other cases;
a matrix C of mutated couples [i.e., couples that mutate either once simultaneously or never] of dimension M×M, the value $C_{i,k}=C_{k,i}$ being equal:
to a second value C1 [for example, "1"] when $A_{i,j}=A_{k,j}$ irrespective of the value of j ranging from 0 to N,
to a first value C2 [for example, "0"] in the other cases;
of determining for a set E of positions a coefficient $R_E$, the value of which is R1 [for example, "1"] when all of the values $B_{i,k}$ are equal to the second value B2, irrespective of the values of i and k belonging to the set E of said positions,
of determining for a set F of positions a coefficient $R_F$, the value of which is R1 [for example, "1"] when all of the values $C_{i,k}$ are equal to the second value C2, irrespective of the values of i and k belonging to the set F of said positions.

The sequences analyzed by the identification preferably comprise a subset of sequences extracted from a databank of nucleotide or polypeptide sequences of pathogenic organisms and most preferentially by nucleotide or polypeptide sequences of pathogenic organisms presenting a high degree of mutability.

According to one embodiment, the subset of sequences comprises all the polypeptide sequences of the different known variants of the protease of the human immunodeficiency virus.

According to another embodiment, the subset of sequences comprises all of the polypeptide sequences of the different known variants of the reverse transcriptase of the human immunodeficiency virus.

According to yet another embodiment, the subset of sequences comprises all of the polypeptide sequences of the different known variants of the integrase of the human immunodeficiency virus.

Another aspect pertains to identifying motifs belonging to pathogenic agents, the nucleic acid and/or polypeptide sequences of which are capable of having mutations.

As a nonlimiting example of such sequences we can cite the sequences of viruses such as the hepatitis C virus which is an RNA virus characterized by the high degree of variability of its genome, with 3% of world prevalence and 600,000 persons infected in France, the Ebola virus which causes hemorrhagic fevers and which is associated with a high mortality rate, the sequences of the flu virus for which it is necessary to develop new vaccines each year or the sequences of other viruses emerging with a high rate of mutability.

Thus, according to a particular aspect, the subset of extracted sequences comprises the polypeptide sequences of the different variants of the neuraminidase of the flu virus.

According to another particular aspect, the subset of extracted sequences comprises all of the polypeptide sequences of the different variants of the hemagglutinin of the flu virus.

Thus, among the sequences of the bacteria capable of having mutations, examples include the C-terminal sequence of the protein HspA of the bacterium *Helicobacter pilori* or the HA-type adhesin of the bacterium *Escherichia coli*.

The methods for identifying motifs are not limited solely to the domain of pathogenic agents. Sets of sequences having motifs which did not mutate simultaneously, or in contrast had mutated together at least once on at least one of the sequences of the set and had never mutated on the other sequences of the set are also presented in other pathologies such as, for example, pathologies in the field of cancer research.

It can be acknowledged that a large percentage of cancers are due to the presence of transposable elements that have a large degree of homology with the viruses, and that the hepatitis B virus is the second identified cause of cancer death after tobacco.

Thus, among the genes implicated in human cancers, capable of having motifs that mutate and for which the set of sequences have sometimes been constituted, we can cite as examples the APC gene which has been essentially implicated in cancer of the colon (Nucleic Acids Res 1998, Jan. 1; 26(1): 269-270, APC gene: database of germline and somatic mutations in human tumors and cell lines. Laurent-Puig P, Beroud C, Soussi T), the gene P53 (Nucleic Acids Res 1997, Jan. 1; 25(1): 138, p. 53 and APC gene mutations: software and databases. Beroud C, Soussi T), MEN-1 (A malignant gastrointestinal stromal tumor in a patient with multiple endocrine neoplasia type 1. Papillon E, Rolachon A, Calender A, Chabre O, Barnoud R, Foumet J), VHL (Mutations of the VHL gene in sporadic renal cell carcinoma: definition of a risk factor for VHL patients to develop an RCC. Gallou C, Joly D, Mejean A, Staroz F, Marin N, Tarlet G, Orfanelli M T, Bouvier R, Droz D, Chretien Y, Marechal J M, Richard S, Junien C, Beroud C), WT1 (Clin Cancer Res 2000, October; 6(10): 3957-65. WT1 splicing alterations in Wilms' tumors. Baudry D, Hamelin M, Cabanis M O, Fournet J C, Toumade M F, Sarnacki S, Junien C, Jeanpierre C).

We also provide for identifying motifs described above for selecting fragments of sequences constituted by and/or comprising motifs that did not mutate simultaneously and/or motifs that mutate simultaneously at least once on at least one sequence of the set and that did not mutate on another sequence of said set for vaccines.

Vaccines are composed of antigens constituted by molecules or parts of molecules of a pathogenic organism which when they are injected in the organism enable production of a larger number of antibodies against the pathogenic organism. These antibodies recognize the molecules against which they are directed and thereby enable the immune system to destroy the pathogenic organism.

There is a nonnegligible lapse of time—often many years—between the moment at which the vaccine is defined and the moment at which it becomes available on the market. For example, with regard to HIV, the high polymerization accuracy of the reverse-transcriptase confers on the virus a high degree of genomic variability which increases as a function of time. The viral population is thus very heterogeneous. Destruction of the wild-type virus by the vaccine leads to the selection of mutant viruses against which the vaccine remains ineffective.

Application of the methods to subsets of variant sequences of the protein sequences of pathogenic sequence makes it possible to trap these mutant virus:
either it mutates but, in this case, it is no longer functional;
or it does not mutate, but then the antibodies produced by the vaccine will be capable of destroying it.

For example, with regard to HIV, the peptides, which comprise the proteins of the virus envelope, identified because they do not mutate together, probably due to genetic pressure, which would cause them to lose their functionality, are vaccine candidates of choice.

In fact, the method for identifying peptide motifs enables selected sequences containing the motifs—either contiguously or not—to prepare a candidate vaccine. The vaccine was as an advantage—in relation to other vaccines developed by conventional means—that it is described in exhaustive manner and contains certain regions necessary for the stability of the vaccine precisely by selection of the sequences that did not mutate simultaneously together, leading to the destruction of the pathogenic organism.

The identification of the motifs that did not mutate simultaneously is more complex for two main reasons:
the number of amino acids not mutating is about ten times larger, and
the combination of amino acids to be tested not being determined in advance, all of the combinations must be envisaged.

We also use fragments of sequences constituted by and/or comprising nucleotide and/or peptide motifs of the analyzed sequences that did not mutate simultaneously and/or motifs that mutate simultaneously at least once on at least one sequence of the set and that not mutate on another sequence of said set for a vaccine.

According to a particular aspect, we use a combination of immunogenic peptides each comprising an amino acid of a motif that did not mutate simultaneously, and selected in the group of immunogenic peptides combination consisting of:

| | |
|---|---|
| VTIKIGGQLK and/or | (SEQ ID NO.10) |
| TIKIGGQLK, | (SEQ ID NO.11) |
| DTVLEEMSL, | (SEQ ID NO.12) |
| LVGPTPVNI and/or | (SEQ ID NO.13) |
| VLVGPTPVNI; | (SEQ ID NO.14) |
| VTLWQRPLV, | (SEQ ID NO.18) |
| VTIKIGGQLK and/or | (SEQ ID NO.10) |
| TIKIGGQLK, and | (SEQ ID NO.11) |
| EEMSLPGRW; | (SEQ ID NO.19) |
| VTIKIGGQLK and/or | (SEQ ID NO.10) |
| TIKIGGQLK, | (SEQ ID NO.11) |
| EEMSLPGRW, and optionally | (SEQ ID NO.19) |
| DTVLEEMSL; | (SEQ ID NO.12) |
| VTIKIGGQLK and/or | (SEQ ID NO.10) |
| TIKIGGQLK, | (SEQ ID NO.11) |
| EEMSLPGRW, | (SEQ ID NO.19) |
| LVGPTPVNI and/or | (SEQ ID NO.13) |
| VLVGPTPVNI, and optionally | (SEQ ID NO.14) |
| DTVLEEMSL; | (SEQ ID NO.12) |
| VTIKGGQLK and/or | (SEQ ID NO.10) |

```
            -continued
TIKLGGQLK,             (SEQ ID NO.11)

EEMSLPGRW,             (SEQ ID NO.19)
and

KMIGGIGGFI;            (SEQ ID NO.20)
and

VTIKIGGQLK             (SEQ ID NO.10)
and/or

TIKIGGQLK,             (SEQ ID NO.11)

EEMSLPGRW,             (SEQ ID NO.19)

LVGPTPVM               (SEQ ID NO.13)
and/or

VLVGPTPVNI,            (SEQ ID NO.14)
and

KMIGGIGGFI;            (SEQ ID NO.20)
and

VTLWQRPLV,             (SEQ ID NO.18)

VTIKIGGQLK             (SEQ ID NO.10)
and/or

TIKIGGQLK,             (SEQ ID NO.11)

EEMSLPGRW,             (SEQ ID NO.19)
and optionally

DTVLEEMSL.             (SEQ ID NO.12)
```

Another aspect also includes methods for identifying motifs or combination of motifs that did not mutate simultaneously and/or that mutate simultaneously at least once on at least one sequence of the set and not having mutated on another sequence of the set to develop diagnostic tools. We further use such identification methods to fragments of sequences constituted by and/or comprising motifs having mutated simultaneously and/or having mutated simultaneously at least once on at least one sequence of the set and not having mutated on another sequence of said set for diagnostic tests.

The methods also make it possible to construct a database, which constitutes a decision-making tool, for example, for determining by the physician of the administration of antiviral therapies to a given patient.

According to another aspect, the method for identifying motifs that did not mutate simultaneously and/or that mutate simultaneously at least once on at least one sequence of the set and not having mutated on another sequence of the set, comprises a supplementary step comprising comparing data linking known drug resistances to observed mutations, for example, in the case of HIV, to the data disclosed by J. Hammond et al. in “Mutations in Retroviral Genes Associated with Drug Resistance.” (The Human Retroviruses and AIDS Compendium, 1999).

The drug-mutated amino acid relationship demonstrated in this manner is very useful for improving treatment. For example, with regard to HIV, comparison of the peptide motifs is performed on three subsets of a protein database, pertaining to reverse transcriptase, protease and integrase provided online by the Division of AIDS of the National Institute of Allergy and Infectious Diseases (NIAID), a part of the National Institutes of Health (NIH).

The comparison of the sequences belonging to the subsets comprising from about 300 to about 8000 sequences or fragments of the sequences of each of these three proteins enables application of the method of the disclosure to identify combinations of amino acids that did not mutate simultaneously and/or that mutate simultaneously at least once on at least one sequence of the set and not having mutated on another sequence of the set.

Thus, the methods make it possible to identify the mutations induced under the pressure of selection.

The aspect comprising comparison with the drug resistances enables selection of a combination of drugs such that the amino acid mutations capable of being induced by each of the antiviral agents, capable of conferring resistance on the various drugs involved in this combination (fewer than ten), are not produced simultaneously. Identification of such motifs enables selection of a drug combination, which disfavors the appearance of more than one mutation at a time, thereby closing the door to multiple resistances. The practitioner can then use the information obtained by applying this method, for example, to isolated viral sequences or viral sequences deduced from the isolated viral genome, of a given patient to ensure that the envisaged multi-drug therapy is in fact the most effective possible. With the identification of a first mutation excluding the two others, a selected three-agent therapy thereby enables the two remaining antiretroviral agents to continue to be effective.

The aspect of identification of peptide regions not having mutated simultaneously and/or that having mutated simultaneously at least once on at least one sequence of the set and not having mutated on another sequence of the set also provides valuable assistance in the case of the appearance of resistances in already treated patients. The methods can, for example, be applied to the subsets of polypeptide sequences among which is included that or those deduced from the sequencing of the isolated viral genome of the patient. Thus, if this genotyping reveals a mutation responsible for resistance, the method of identification of peptide motifs not having mutated allows implementation of a multiple-therapy regimen designed to maintain the selection pressure on the mutation. The molecule identified in this manner can be accompanied by two or three antiretroviral agents, which target domains of the protein not capable of mutating at the same time as the zone that mutated.

Such methods are useful for the implementation of new antiretroviral combinations maximally preventing therapeutic escape. Thus, for example, identification of motifs within a given gene having mutated at least once simultaneously on at least one variant and not having mutated on other variants, enables identification of regions of the gene, which could present a physical or functional interaction. In contrast, identification of motifs not having mutated simultaneously enables identification of regions of the gene whose mutual presence is essential and indispensable for its function.

We also provide for identification of a set of genes or a set of non coding sequences of motifs not having mutated simultaneously. Identification of such motifs enables selection of genetic regions that can have physical or functional interactions on the overall genome.

Another aspect relates to methods for identifying motifs and combinations of motifs for selecting fragments constituted by and/or comprising motifs not having mutated simultaneously for the preparation of therapeutic targets.

Still another aspect pertains to the use of fragments of sequences constituted by and/or comprising motifs either having mutated at least once on at least one sequence of the set and not having mutated on the other sequences of the set for the preparation of therapeutic targets.

We also use motifs or combinations of motifs identified in this manner for preparing therapeutic targets that are useful for screening new therapeutic compounds to prevent and/or treat human, animal or plant pathologies. Thus, the preparation, after having identified motifs not having mutated simultaneously, or sequence fragments containing them, enables preparation of a binding site against which will be tested therapeutic compounds directed against the pathogenic organism and especially therapeutic compounds against which the wild-type pathogenic organism can not develop resistance mutations.

According to a particular aspect, we use motifs or combinations of motifs identified in this manner for preparing therapeutic targets that are useful for screening new compounds to prevent and/or to treat HIV.

As an example, we use of HIV protease motifs or combinations of motifs of amino acids that do not mutate simultaneously selected in the group consisting of positions (36, 37, 39, 41, 60, 77), (70, 13, 67, 69, 93, 71, 72), (10, 12), (14, 19, 20), (64, 63, 18, 17, 15, 62, 73, 69, 71, 72, 89, 68), (77, 76, 32, 57, 33, 35, 36, 83), (30, 73, 90, 84, 76, 32, 47), (15, 63, 64, 62, 66, 65), (19, 14, 16, 13), (13, 19, 85, 68), (45, 48, 58), (73, 64, 92, 88, 30), (65, 15, 69, 71, 93), (32, 30, 74, 57, 77), (24, 90), (20, 14, 19, 16, 13, 85, 68, 64, 63, 18, 17, 62, 15, 66, 65, 69, 93, 71, 70, 67, 72, 89), and (73, 92, 24, 90, 88, 84, 76, 30, 32, 57, 47, 74, 77, 83, 33, 35, 36, 37, 39, 41, 60) as reference to the ancestral sequence of the B sub-type of the HIV protease sequence (SEQ ID NO.15) for preparing binding sites that are useful for screening new compounds to prevent and/or to treat HIV.

As another example, we use HIV protease motifs or combinations of motifs that did not mutate simultaneously and/or of the motifs having mutated simultaneously at least once on at least one of the sequences of the set and not having mutated on the other sequences of the set selected in the group consisting of positions (4, 5, 6, 7, 8), (10, 22, 24, 83, 84), (10, 22, 83, 84, 85), (10, 23, 82, 84, 85), (22, 33, 83, 84, 85), (23, 33, 82, 84, 85), (60, 61, 62, 63, 72), (60, 62, 63, 72, 73), (61, 62, 63, 71, 72), (62, 63, 71, 72, 73), (3, 4, 5, 8), (10, 11, 13, 22), (10, 11, 22, 24), (10, 11, 22, 85), (10, 13, 22, 83), (11, 13, 66, 67), (13, 14, 66, 67), (13, 66, 67, 69), (20, 33, 34, 83), (32, 33, 34, 82), (32, 33, 82, 85), (33, 34, 82, 84), (33, 34, 83, 84), (39, 60, 61, 62), (46, 47, 53, 54), (46, 48, 53, 54), (46, 53, 54, 55), (66, 71, 90, 93), and (71, 72, 88, 93) as reference to the HIV-1 B subtype ancestral protease sequence (SEQ ID NO.15) for the development of new therapeutic targets.

The selection of fragments constituted by and/or comprising motifs not having mutated simultaneously or having mutated simultaneously at least once on at least one of the sequences of the set and not having mutated on the other sequences of the set is, thus, useful for the preparation of diagnostic tools since it is not always easy to detect rapidly a certain type of or subtype of pathogenic organism, because the identification of peptide motifs according to aspects of the disclosure enables preparation of fragments of peptides comprising the motifs most representative of a subtype of a pathogenic organism. These fragments are then used in detection tests such as, for example, immunoenzyme tests.

This application of the methods comprises identifying a set of motifs indispensable for the function of a protein of a human, animal or plant organism or of a pathogenic organism. These motifs can constitute, for example, a subset of amino acids known to play an important role in the function of the targeted protein. The motifs identified in this manner are advantageously contiguous motifs of the genetic sequence and represent a linear sequence of the gene. The motifs identified are advantageously motifs noncontiguous on the linear sequence of the gene. They can then be useful for completing three-dimensional analysis studies to confirm a possible nonlinear spatial proximity of the motifs. The methods can then include a new supplementary step (d) after the step (c) of identification of the motifs, the step comprising comparing the motifs with the three-dimensional structural data of these proteins such as the amino acids involved in the catalytic site and/or in the sites linked by noncompetitive inhibitors. This latter comparison produces a list of amino acids involved in the protein function and not having mutating together and/or having mutated simultaneously at least once on at least one sequence of the set and not having mutated on another sequence of said set.

We also use fragments of sequences constituted by and/or comprising peptide motifs having mutated simultaneously for the development of diagnostic tools. The method for the identification of peptide regions defines the most representative peptides of a subtype. Once they are identified, these peptides are used in detection tests known in the art, such as, for example, immunoenzyme tests of the ELISA type.

The search for peptides representing a subtype of a particular type is performed as indicated above. It is a question of finding peptide antigens capable of being recognized by a particular serum containing or not containing the antibodies of a particular subtype. The methods can be applied to any databank of sequences. The results are compared by subtypes and the theoretical peptide combination the most representative of a particular pathogenic type is thereby identified. The peptides identified in this manner are synthesized and tested immunologically against a collection of serums.

The methods exhibit their value especially when used for the identification either of motifs having mutated once together or not having mutated, from a large number of sequences comprising a large number of motifs to select the sequences of motifs useful for the various applications envisaged above.

This disclosure will be understood more clearly on reading the description of the experimental studies performed in the context of the research carried out by the applicants, which should not be interpreted as being limiting in nature.

Example 1

To illustrate the methods for the identification of motifs, the example below shows the different matrices constituted in a comparison of motifs performed on a subset of eight sequences based on the reference sequence S V R L G H K D E V (SEQ ID NO.1). The peptides that follow are shown in SEQ ID NOs 1-9, respectively, in order of appearance.

| POSITIONS | 0 1 2 3 4 5 6 7 8 9 |
|---|---|
| Reference sequence (consensus) | S V R L G H K D E V |
| Subset of sequences | Alignment |
| SEQ ID NO.2 | S R R L G H K D E V |
| SEQ ID NO.3 | S V R L G H K L E V |
| SEQ ID NO.4 | S R D L G H K D E V |
| SEQ ID NO.5 | S V R L G H L D V V |
| SEQ ID NO.6 | S V D L G H K T E V |
| SEQ ID NO.7 | S K R L G H K D E V |
| SEQ ID NO.8 | S V R L G H G D G V |
| SEQ ID NO.9 | S V R L G H K S E V |

1. Mutation Matrix A

Attributed values:

A1=0, if motif mutated in relation to the reference sequence

A2=1, if another case (motif not mutated in relation to the reference sequence).

| POSITION | 0 1 2 3 4 5 6 7 8 9 |
|---|---|
| SEQ ID NO. 2 | 1 0 1 1 1 1 1 1 1 1 |
| SEQ ID NO. 3 | 1 1 1 1 1 1 1 0 1 1 |
| SEQ ID NO. 4 | 1 0 0 1 1 1 1 1 1 1 |
| SEQ ID NO. 5 | 1 1 1 1 1 1 0 1 0 1 |
| SEQ ID NO. 6 | 1 1 0 1 1 1 1 0 1 1 |
| SEQ ID NO. 7 | 1 0 1 1 1 1 1 1 1 1 |
| SEQ ID NO. 8 | 1 1 1 1 1 1 0 1 0 1 |
| SEQ ID NO. 9 | 1 1 1 1 1 1 1 0 1 1 |

2. Nonmutated Matrix B

Attributed values:

B1=0, if any individual couple of motifs mutated simultaneously

B2=1, if another case (e.g. couple of motifs never having had mutated simultaneously)

| POSITION | 0 1 2 3 4 5 6 7 8 9 |
|---|---|
| POS0 | 1 1 1 1 1 1 1 1 1 1 |
| POS1 | 1 0 0 1 1 1 1 1 1 1 |
| POS2 | 1 0 0 1 1 1 1 0 1 1 |
| POS3 | 1 1 1 1 1 1 1 1 1 1 |
| POS4 | 1 1 1 1 1 1 1 1 1 1 |
| POS5 | 1 1 1 1 1 1 1 1 1 1 |
| POS6 | 1 1 1 1 1 1 0 1 0 1 |
| POS7 | 1 1 0 1 1 1 1 0 1 1 |
| POS8 | 1 1 1 1 1 1 0 1 0 1 |
| POS9 | 1 1 1 1 1 1 1 1 1 1 |

3. Mutated Matrix C

Attributed values:

C1=1, if a couple of motifs mutated simultaneously and no motif mutated alone,

C2=0, other cases.

| POSITION | 0 1 2 3 4 5 6 7 8 9 |
|---|---|
| POS0 | 0 0 0 0 0 0 0 0 0 0 |
| POS1 | 0 0 0 0 0 0 0 0 0 0 |
| POS2 | 0 0 0 0 0 0 0 0 0 0 |
| POS3 | 0 0 0 0 0 0 0 0 0 0 |
| POS4 | 0 0 0 0 0 0 0 0 0 0 |
| POS5 | 0 0 0 0 0 0 0 0 0 0 |
| POS6 | 0 0 0 0 0 0 0 0 1 0 |
| POS7 | 0 0 0 0 0 0 0 0 0 0 |
| POS8 | 0 0 0 0 0 0 1 0 0 0 |
| POS9 | 0 0 0 0 0 0 0 0 0 0 |

The interrogation of the mutated matrix C thus makes it possible to identify the motifs in positions 6 and 8 as motifs having mutated at least once together.

Example 2

To further illustrate the methods for identification of motifs, the example below shows the use of the method on the subtype B HIV protease.

1. HIV Protease Sequences Alignment:

In this analysis, an alignment of 24155 different subtype B HIV protease protein sequences have been compared with three different reference sequences. These three reference sequences correspond to the ancestral sequence (SEQ ID NO.15), which has been phylogenetically calculated, the consensus sequence for this 24155 sequences alignment (SEQ ID NO.16), and the HXB2 (SEQ ID NO.17) considered as the historical reference.

2. Identification of New Therapeutic Targets in HIV Protease:

To identify new therapeutic targets on HIV protease protein, we searched for amino acids couples that always vary simultaneously in the above described alignment with the method described in the example 1. 556 amino acids couples, which always vary simultaneously, have been identified.

The term "to vary" as used herein is understood to mean the motifs that did not mutate simultaneously and/or the motifs having mutated simultaneously at least once on at least one of the sequences of the set and not having mutated on the other sequences of the set.

Thus, we identified the amino distant from less than 10 Angstroms in these 556 amino acids couples. For this identification, the distance between amino acids has been calculated from the HIV protease 3D structure (PDB:1HSG). This analysis has allowed the identification of 90 amino acids couples.

Finally, we searched for maximal cliques. This analysis has allowed the identification of 29 cliques of amino acids positions, which vary simultaneously. The results are shown in table 1.

TABLE 1

| Group | Maximal cliques of the amino acids, which vary simultaneously and distant from less than 10 Angstroms (with reference to the ancestral protease sequence) |
|---|---|
| 1 | (4, 5, 6, 7, 8) |
| 2 | (10, 22, 24, 83, 84) |
| 3 | (10, 22, 83, 84, 85) |
| 4 | (10, 23, 82, 84, 85) |
| 5 | (22, 33, 83, 84, 85) |
| 6 | (23, 33, 82, 84, 85) |
| 7 | (60, 61, 62, 63, 72) |
| 8 | (60, 62, 63, 72, 73) |
| 9 | (61, 62, 63, 71, 72) |
| 10 | (62, 63, 71, 72, 73) |
| 11 | (3, 4, 5, 8) |
| 12 | (10, 11, 13, 22) |
| 13 | (10, 11, 22, 24) |
| 14 | (10, 11, 22, 85) |
| 15 | (10, 13, 22, 83) |
| 16 | (11, 13, 66, 67) |
| 17 | (13, 14, 66, 67) |
| 18 | (13, 66, 67, 69) |
| 19 | (20, 33, 34, 83) |
| 20 | (32, 33, 34, 82) |
| 21 | (32, 33, 82, 85) |
| 22 | (33, 34, 82, 84) |
| 23 | (33, 34, 83, 84) |
| 24 | (39, 60, 61, 62) |
| 25 | (46, 47, 53, 54) |
| 26 | (46, 48, 53, 54) |
| 27 | (46, 53, 54, 55) |
| 28 | (66, 71, 90, 93) |
| 29 | (71, 72, 88, 93) |

Consequently, the method allowed the identification of twenty nine potential targets for developing therapies within the HIV protease.

3. Identification of Potential Binding Site for New Drug Against HIV Protease:

To identify potential binding site for new drugs in subtype B HIV protease protein, we searched for amino acids couples that never mutate simultaneously in the above described alignment with the method described in the Example 1. Then, we selected the amino acids, which are distant from less than 10 Angstroms. For this identification, the distance between amino acids was calculated from the HIV protease 3D structure as described previously.

The results of this analysis are shown in table 2.

TABLE 2

| Group | Combinations of the amino acids, which never mutate simultaneously and distant from less than 10 Angstroms (with reference to the ancestral protease sequence) |
|---|---|
| 1 | (36, 37, 39, 41, 60, 77) |
| 2 | (70, 13, 67, 69, 93, 71, 72) |
| 3 | (10, 12) |
| 4 | (14, 19, 20) |
| 5 | (64, 63, 18, 17, 15, 62, 73, 69, 71, 72, 89, 68) |
| 8 | (77, 76, 32, 57, 33, 35, 36, 83) |
| 9 | (30, 73, 90, 84, 76, 32, 47) |
| 10 | (15, 63, 64, 62, 66, 65) |
| 11 | (19, 14, 16, 13) |
| 12 | (13, 19, 85, 68) |
| 14 | (45, 48, 58) |
| 15 | (73, 64, 92, 88, 30, 76) |
| 16 | (65, 15, 69, 71, 93) |
| 17 | (32, 30, 74, 57, 77) |
| 18 | (24, 90) |
| 19 | (20, 14, 19, 16, 13, 85, 68, 64, 63, 18, 17, 62, 15, 66, 65, 69, 93, 71, 70, 67, 72, 89) |
| 20 | (73, 92, 24, 90, 88, 84, 76, 30, 32, 57, 47, 74, 77, 83, 33, 35, 36, 37, 39, 41, 60) |

The position indicated in bold correspond to amino acids implicated in drug resistance.

Consequently, the method allowed the identification of twenty binding sites for developing new drugs within the HIV protease.

4. Identification of Potential Stable Combinations of Antigenic Sites for New Vaccine Against HIV:

To identify a new vaccine against HIV protease comprising immunogenic peptides having a better efficiency, we searched for all amino acids couples that never mutate simultaneously in the above described alignment with the method described in the Example 1. Then, the motifs comprising the identified amino acids were compared with a library of described HIV protease epitopes provided online by the Division of AIDS of the National Institute of Allergy and Infectious Diseases (NIAID) a part of the National Institutes of Health (NIH) to select immunogenic peptides each comprising one amino acid of the identified motif.

The results are shown in table 3.

TABLE 3

| Group of positions which never mutate simultaneously | Position of the amino acids, which never mutate simultaneously (with reference to the ancestral protease sequence) | Identified HIV protease epitope comprising said amino acid |
|---|---|---|
| 1 | 15 | A3 supertype (VTIKIGGQLK; SEQ ID NO. 10) (TIKIGGQLK; SEQ ID NO. 11) |

TABLE 3-continued

| Group of positions which never mutate simultaneously | Position of the amino acids, which never mutate simultaneously (with reference to the ancestral protease sequence) | Identified HIV protease epitope comprising said amino acid |
|---|---|---|
| | 33 | A68, A*6802 (DTVLEEMSL; SEQ ID NO. 12) |
| | 77 | A2 supertype, A2, A02, A*0201 (LVGPTPVNI; SEQ ID NO. 13) (VLVGPTPVNI; SEQ ID NO. 14) |
| 2 | 10 | A74 (VTLWQRPLV; SEQ ID NO. 18) |
| | 14 | A3 supertype (VTIKIGGQLK; SEQ ID NO. 10) (TIKIGGQLK; SEQ ID NO. 11) |
| | 19 | A3 supertype (VTIKIGGQLK; SEQ ID NO. 10) (TIKIGGQLK; SEQ ID NO. 11) |
| | 39 | B44 (EEMSLPGRW; SEQ ID NO. 19) |
| 3 | 12 | A3 supertype (VTIKIGGQLK; SEQ ID NO. 10) (TIKIGGQLK; SEQ ID NO. 11) |
| | 36 | A68, B44 (DTVLEEMSL; SEQ ID NO. 12) (EEMSLPGRW; SEQ ID NO. 19) |
| | 37 | A 68, B44 (DTVLEEMSL; SEQ ID NO. 12) (EEMSLPGRW; SEQ ID NO. 19) |
| | 39 | B44 (EEMSLPGRW; SEQ ID NO. 19) |
| 4 | 12 | A3 supertype (VTIKIGGQLK; SEQ ID NO. 10) (TIKIGGQLK; SEQ ID NO. 11) |
| | 37 | A 68, B44 (DTVLEEMSL; SEQ ID NO. 12) (EEMSLPGRW; SEQ ID NO. 19) |
| | 39 | B44 (EEMSLPGRW; SEQ ID NO. 19) |
| | 82 | A02, A*0201 (LVGPTPVNI; SEQ ID NO. 13) (VLVGPTPVNI; SEQ ID NO. 14) |
| 5 | 14 | A3 supertype (VTIKIGGQLK; SEQ ID NO. 10) (TIKIGGQLK; SEQ ID NO. 11) |
| | 19 | A3 supertype (VTIKIGGQLK; SEQ ID NO. 10) (TIKIGGQLK; SEQ ID NO. 11) |
| | 36 | B44 (EEMSLPGRW; SEQ ID NO. 19) |
| | 39 | B44 (EEMSLPGRW; SEQ ID NO. 19) |

TABLE 3-continued

| Group of positions which never mutate simultaneously | Position of the amino acids, which never mutate simultaneously (with reference to the ancestral protease sequence) | Identified HIV protease epitope comprising said amino acid |
|---|---|---|
| 6 | 14 | A3 supertype (VTIKIGGQLK; SEQ ID NO. 10) (TIKIGGQLK; SEQ ID NO. 11) |
| | 20 | A3 supertype (VTIKIGGQLK; SEQ ID NO. 10) (TIKIGGQLK; SEQ ID NO. 11) |
| | 39 | B44 (EEMSLPGRW; SEQ ID NO. 19) |
| | 41 | B44 (EEMSLPGRW; SEQ ID NO. 19) |
| 7 | 14 | A3 supertype (VTIKIGGQLK; SEQ ID NO. 10) (TIKIGGQLK; SEQ ID NO. 11) |
| | 39 | B44 (EEMSLPGRW; SEQ ID NO. 19) |
| | 41 | B44 (EEMSLPGRW; SEQ ID NO. 19) |
| | 54 | A2 supertype (KMIGGIGGFI; SEQ ID NO. 20) |
| 8 | 10 | A74 (VTLWQRPLV; SEQ ID NO. 18) |
| | 12 | A3 supertype (VTIKIGGQLK; SEQ ID NO. 10) (TIKIGGQLK; SEQ ID NO. 11) |
| | 37 | A68/B44 (DTVLEEMSL; SEQ ID NO. 12) (EEMSLPGRW; SEQ ID NO. 19) |

TABLE 3-continued

| Group of positions which never mutate simultaneously | Position of the amino acids, which never mutate simultaneously (with reference to the ancestral protease sequence) | Identified HIV protease epitope comprising said amino acid |
|---|---|---|
| | 39 | B44 (EEMSLPGRW; SEQ ID NO. 19) |
| 9 | 12 | A3 supertype (VTIKIGGQLK; SEQ ID NO. 10) (TIKIGGQLK; SEQ ID NO. 11) |
| | 18 | A3 supertype (VTIKIGGQLK; SEQ ID NO. 10) (TIKIGGQLK; SEQ ID NO. 11) |
| | 35 | A68, B44 (DTVLEEMSL; SEQ ID NO. 12) (EEMSLPGRW; SEQ ID NO. 19) |
| | 39 | B44 (EEMSLPGRW; SEQ ID NO. 19) |
| 10 | 14 | A3 supertype (VTIKIGGQLK; SEQ ID NO. 10) (TIKIGGQLK; SEQ ID NO. 11) |
| | 39 | B44 (EEMSLPGRW; SEQ ID NO. 19) |
| | 48 | A2 supertype (KMIGGIGGFI; SEQ ID NO. 20) |
| | 76 | A02, A*0201 (LVGPTPVNI; SEQ ID NO. 13) HLA-A*0201 (VLVGPTPVNI; SEQ ID NO. 14) |

Consequently, the method allowed the identification of multiple amino acids in HIV protease sequence, which do not mutate simultaneously, and present in ten combinations of four or three distinct epitopes.

The invention claimed is:

1. A method for identifying a combination of motifs which do not mutate simultaneously in a set of sequences and which correspond to a potential drug target on a viral polypeptide or a potential drug binding site for docking on a viral polypeptide comprising:

a) selecting a set of viral sequences from a databank of viral polypeptides, b) aligning the set of viral sequences of ordered motifs represented by a single-character code on a programmed computer using a multiple sequence alignment program, c) comparing a reference viral sequence with the set of aligned viral sequences by, forming a first numerical matrix A of dimensions N×M in which N designates a number of viral sequences and M designates a number of motifs of one viral sequence of said alignment, with value $A_{i,j}$ being equal to a first value A1 when the motif of position i of viral sequence j with a value ranging from 0 to N is mutated in relation to a motif of position i of the reference viral sequence and equal to a second value A2 in other cases, forming two analysis matrices B and C of mutations in which:

a matrix B of unmutated couples, of couples which do not mutate simultaneously, of dimension M×M, value $B_{i,k}=B_{k,i}$ being equal:

to a first value B1 when $A_{i,j}=A_{k,j}=A1$ irrespective of the value of j ranging from 0 to N, to a second value B2 in other cases;

a matrix C of mutated couples of dimension M×M, value $C_{k,i}=C_{i,k}$ being equal:

to a second value C1 when $A_{i,j}=A_{k,j}$ irrespective of the value of j ranging from 0 to N, to a first value C2 in other cases;

determining for a set E of positions a coefficient $R_E$ whose value is $R_1$ when values $B_{i,k}$ are equal to a second value B2, irrespective of the values of i and k belonging to set E of said positions, determining for a set F of positions, a coefficient $R_F$, the value of which is $R_1$ when values $C_{i,k}$ are equal to second value C2, irrespective of the values of i and k belonging to set F of said position; wherein the matrices i and k designate positions and j designates a sequence;

d) identifying motifs not having mutated simultaneously or motifs having mutated simultaneously at least once on at least one sequence of the set and not having mutated on another sequence of said set, e) selecting a combination of the identified motifs which are less than 20 Å apart in a three-dimensional structure of the viral polypeptide, and f) identifying the selected combination of motifs, wherein the selected combination of motifs is a combination of amino acid residues;

whereby said method allows the identification of motifs corresponding to a potential drug target on a viral polypeptide or a potential drug binding site for docking on a viral polypeptide.

2. The method according to claim 1, wherein the reference viral sequence is a wild-type viral sequence.

3. The method according to claim 1, wherein the reference viral sequence is an amino acid sequence comprising in a position i a motif present in position i in a predetermined number of sequences of step (a).

4. The method according to claim 1, wherein positions of the sets E and/or F are designated by the user.

5. The method according to claim 1, wherein steps (c) and (d) further comprise a test step including generating a totality of combinations of possible positions, determining for each of said combinations the value of coefficients $R_R$ or $R_F$, and retaining the combination corresponding to a largest set of positions coefficient $R_E$ or $R_F$ of which corresponds to said second value.

6. The method according to claim 1, wherein the set of viral sequences comprises sequences of motifs from a pathogenic virus having a high level of mutability.

7. The method according to claim 1, wherein the set of viral sequences comprises sequences of motifs of viral genes involved in human, animal or plant pathologies and having a high level of mutability.

8. The method according to claim 1, wherein the set of sequences of step (a) comprises all polypeptide sequences of different variants of a protease of human immunodeficiency virus.

9. The method according to claim 1, further comprising, after step (d), a step (g) of comparing motifs identified in step (d) with known drug resistances to observed mutations.

10. The method according to claim 1, further comprising, after step (d), a step (g) of comparing motifs identified in step (d) with motifs of sequences implicated in a catalytic site and/or in sites linked by noncompetitive inhibitors.

11. A method of identifying HIV protease sequences with increased susceptibilities to protease inhibitors comprising:
a) selecting a set of HIV protease sequences from a databank of HIV protease polypeptides,
b) aligning the set of HIV protease sequences of ordered motifs represented by a single-character code on a programmed computer using a multiple sequence alignment program where the sequences are the amino acid sequences of an HIV protease,
c) comparing a reference HIV protease sequence with the set of aligned HIV protease sequences by,
forming a first numerical matrix A of dimensions N×M in which N designates a number of HIV protease sequences and M designates a number of motifs of one HIV protease sequence of said alignment with value $A_{i,j}$ being equal to a first value A1 when the motif of position i of HIV protease sequence j with a valve ranging from 0 to N is mutated in relation to a motif of position i of the reference HIV protease sequence and equal to a second value A2 in other cases,
forming two analysis matrices B and C of mutations in which:
a matrix B of unmutated couples, of couples which do not mutate simultaneously, of dimension M×M, value $B_{i,k}=B_{k,i}$ equal:
to a first value B1 when $A_{i,j}=A_{k,j}=A1$ irrespective of the value of j ranging from 0 to N,
to a second value B2 in other cases;
a matrix C of mutated couples of dimension M×M, value $C_{k,i}=C_{i,k}$ being equal:
to a second value C1 when $A_{i,j}=A_{k,j}$ irrespective of the value of j ranging from 0 to N,
to a first value C2 in other cases;

determining for a set E of positions a coefficient $R_E$ whose value is $R_1$ when values $B_{i,k}$ are equal to a second value B2, irrespective of the values of i and k belonging to set E of said positions, determining for a set F of positions, a coefficient $R_F$, the value of which is $R_1$ when values $C_{i,k}$ are equal to second value C2, irrespective of the values of i and k belonging to set F of said position; wherein the matrices i and k designate positions and j designates a HIV protease sequence;

d) identifying motifs not having mutated simultaneously or motifs having mutated simultaneously at least once on at least one sequence of the set and not having mutated on another sequence of said set, e) selecting a combination of the identified motifs which are less than 20 apart in a three-dimensional structure of the HIV protease polypeptide, f) identifying the selected combination of motifs, wherein the identified combination of motifs is a combination of amino acid residues, and g) comparing the measured inhibition of an aligned HIV protease containing at least one motif in the identified combination of motifs by an inhibitor and the measured inhibition of a reference HIV protease by an inhibitor, where the inhibitor binds at least one motif in the identified combination of motifs;

wherein said comparison results in the identification of HIV protease sequences with increased susceptibility to protease inhibitors.

12. A method of identifying HIV protease sequences with increased susceptibilities to protease inhibitors comprising:
a) selecting a set of HIV protease sequences from a databank of HIV protease polypeptides,
b) aligning the set of HIV protease sequences of ordered motifs represented by a single-character code on a programmed computer using a multiple sequence alignment program where the sequences are the amino acid sequences of an HIV protease,
c) comparing a reference HIV protease sequence with the set of aligned HIV protease sequences by,
forming a first numerical matrix A of dimensions N×M in which N designates a number of HIV protease sequences and M designates a number of motifs of one HIV protease sequence of said alignment, with value $A_{i,j}$ being equal to a first value A1 when the motif of position i of HIV protease sequence j with a valve ranging from 0 to N is mutated in relation to a motif of position i of the reference HIV protease sequence and equal to a second value A2 in other cases, forming two analysis matrices B and C of mutations in which:

a matrix B of unmutated couples, of couples which do not mutate simultaneously, of dimension M×M, value $B_{i,k}=B_{k,i}$ being equal:

to a first value B1 when $A_{i,j}=A_{k,j}=A1$ irrespective of the value of j ranging from 0 to N, to a second value B2 in other cases;

a matrix C of mutated couples of dimension M×M, value $C_{k,i}=C_{i,k}$ being equal:

to a second value C1 when $A_{i,j}=A_{k,j}$ irrespective of the value of j ranging from 0 to N, to a first value C2 in other cases;

determining for a set E of positions a coefficient $R_E$ whose value is $R_1$ when values $B_{i,k}$ are equal to a second value B2, irrespective of the values of i and k belonging to set E of said positions, determining for a set F of positions a coefficient $R_F$, the value of which is $R_1$ when values $C_{i,k}$ are equal to second value C2, irrespective of the values of i and k belonging to set F of said position; wherein the matrices i and k designate positions and j designates a HIV protease sequence:

d) identifying motifs not having mutated simultaneously or motifs having mutated simultaneously at least once on at least one sequence of the set and not having mutated on another sequence of said set, e) identifying a combination of motifs which do not mutate simultaneously in the set of HIV protease sequences, f) selecting a combination of the identified motifs which are less than 20 Å apart in a three-dimensional structure of the HIV protease polypeptide, g) identifying the selected combinations of motifs, wherein the identified combination of motifs is a combination of amino acid residues, and h) comparing the measured inhibition of an aligned HIV protease containing at least one motif in the identified combination of motifs by an inhibitor and the measured inhibition of a reference HIV protease by an inhibitor, where the inhibitor binds at least one motif in the identified combination of motifs;

wherein said comparison results in the identification of HIV protease sequences with increased susceptibility to protease inhibitors.

13. The method of claim 12 wherein steps (a), (b), (c), (d), (e) and (f) are computerized.

14. A method for identifying a combination of motifs which do not mutate simultaneously in a set of sequences and which correspond to a potential drug target on a viral polypeptide or a potential drug binding site for docking on a viral polypeptide comprising:

a) selecting a set of viral sequences from a databank of viral polypeptides, b) aligning the set of viral sequences of ordered motifs represented by a single-character code on a programmed computer using a multiple sequence alignment program, c) comparing a reference viral sequence with the set of viral sequences aligned in step (b) by forming a first numerical matrix A of dimensions N×M in which N designates a number of viral sequences and M designates a number of motifs of one viral sequence of said alignment, with value $A_{i,j}$ being equal to a first value A1 when the motif of position i of viral sequence j with a value ranging from 0 to N is mutated in relation to a motif of position i of the reference viral sequence and equal to a second value A2 in other cases, forming two analysis matrices B and C of mutations in which:

a matrix B of unmutated couples, of couples which do not mutate simultaneously, of dimension M×M, value $B_{i,k}=B_{k,i}$ being equal:

to a first value B1 when $A_{i,j}=A_{k,j}=A1$ irrespective of the value of j ranging from 0 to N, to a second value B2 in other cases;

a matrix C of mutated couples of dimension M×M, value $C_{k,i}=C_{i,k}$ being equal:

to a second value C1 when $A_{i,j}=A_{k,j}$ irrespective of the value of j ranging from 0 to N, to a first value C2 in other cases;

determining for a set E of positions a coefficient $R_E$ whose value is $R_1$ when values $B_{i,k}$ are equal to a second value B2, irrespective of the values of i and k belonging to set E of said positions, determining for a set F of positions, a coefficient $R_F$, the value of which is $R_1$ when values $C_{i,k}$ are equal to second value C2, irrespective of the values of i and k belonging to set F of said position; wherein the matrices i and k designate positions and j designates a sequence, d) identifying motifs not having mutated simultaneously or motifs having mutated simultaneously at least once on at least one sequence of the set and not having mutated on another sequence of said set, e) selecting a combination of the motifs identified in step (d) which are less than 20 Å apart in a three-dimensional structure of the viral polypeptide, and f) identifying the selected combination of motifs, wherein the selected combination of motifs is a combination of amino acid residues;

whereby said method allows the identification of motifs corresponding to a potential drug target on a viral polypeptide or a potential drug binding site for docking on a viral polypeptide.

15. A method of identifying a stable target on HIV protease sequences with increased susceptibilities to protease inhibitors comprising:

a) selecting a set of HIV protease sequences from a databank of HIV protease polypeptides, b) aligning the set of HIV protease sequences of ordered motifs represented by a single-character code on a programmed computer using a multiple sequence alignment program where the sequences are the amino acid sequences of an HIV protease, c) comparing a reference HIV protease sequence with the set of HIV protease sequences aligned in step (b) forming a first numerical matrix A of dimensions N×M in which N designates a number of viral sequences and M designates a number of motifs of one viral sequence of said alignment, with value $A_{i,j}$ being equal to a first value A1 when the motif of position i of viral sequence j with a value ranging from 0 to N is mutated in relation to a motif of position i of the reference viral sequence and equal to a second value A2 in other cases, forming two analysis matrices B and C of mutations in which:

a matrix B of unmutated couples, of couples which do not mutate simultaneously, of dimension M×M, value $B_{i,k}=B_{k,i}$ being equal:

to a first value B1 when $A_{i,j}=A_{k,j}=A1$ irrespective of the value of j ranging from 0 to N, to a second value B2 in other cases;

a matrix C of mutated couples of dimension M×M, value $C_{k,i}=C_{i,k}$ being equal:

to a second value C1 when $A_{i,j}=A_{k,j}$ irrespective of the value of j ranging from 0 to N, to a first value C2 in other cases;

determining for a set E of positions a coefficient $R_E$ whose value is $R_1$ when values $B_{i,k}$ are equal to a second value B2, irrespective of the values of i and k belonging to set E of said positions, determining for a set F of positions, a coefficient $R_F$, the value of which is $R_1$ when values $C_{i,k}$ are equal to second value C2, irrespective of the values of i and k belonging to set F of said position; wherein the matrices i and k designate positions and j designates a sequence, d) identifying motifs not having mutated simultaneously or motifs having mutated simultaneously at least once on at least one sequence of the set and not having mutated on another sequence of said set, e) selecting a combination of the motifs identified in step (d) which are less than 20 Å apart in a three-dimensional structure of the HIV protease polypeptide, f) identifying the selected combination of motifs, wherein the identified combination of motifs is a combination of amino acid residues and said combination of amino acid residues are the said stable target on the HIV protease sequences with increased susceptibility to protease inhibitors, whereby said method results in the identification of a stable target on HIV protease sequences with increased susceptibility to protease inhibitors.

* * * * *